United States Patent
Haley et al.

(10) Patent No.: US 9,964,531 B2
(45) Date of Patent: *May 8, 2018

(54) PHENYLACETYLENES

(71) Applicant: University of Oregon, Eugene, OR (US)

(72) Inventors: Michael M. Haley, Eugene, OR (US); Darren W. Johnson, Eugene, OR (US); Jeff Engle, Eugene, OR (US); Calden Carroll, Eugene, OR (US)

(73) Assignee: University of Oregon, Eugene, OR (US)

( * ) Notice: Subject to any disclaimer, the term of this patent is extended or adjusted under 35 U.S.C. 154(b) by 185 days.

This patent is subject to a terminal disclaimer.

(21) Appl. No.: 14/760,696

(22) PCT Filed: Jan. 21, 2014

(86) PCT No.: PCT/US2014/012303
§ 371 (c)(1),
(2) Date: Jul. 13, 2015

(87) PCT Pub. No.: WO2014/116578
PCT Pub. Date: Jul. 31, 2014

(65) Prior Publication Data
US 2015/0355153 A1    Dec. 10, 2015

Related U.S. Application Data

(60) Provisional application No. 61/755,773, filed on Jan. 23, 2013.

(51) Int. Cl.
*C07D 213/61* (2006.01)
*C07D 213/73* (2006.01)
(Continued)

(52) U.S. Cl.
CPC ....... *G01N 33/182* (2013.01); *C07D 207/335* (2013.01); *C07D 213/36* (2013.01);
(Continued)

(58) Field of Classification Search
None
See application file for complete search history.

(56) References Cited

U.S. PATENT DOCUMENTS 7,803,946 B2   9/2010 Haley et al.
8,841,460 B2   9/2014 Johnson et al.
(Continued)

OTHER PUBLICATIONS

Carroll Stimpson, C. N. "Functionalized 2,6-Bis-(anilinoethynyl) Pyridine: Anion-Mediated Self-Assembly and Chemosensing," Dissertation, University of Oregon, Dec. 2011.*

(Continued)

*Primary Examiner* — Yelena G Gakh
*Assistant Examiner* — Michelle Adams
(74) *Attorney, Agent, or Firm* — Hickman Palermo Becker Bingham LLP

(57) ABSTRACT

Disclosed herein are host or receptor compounds that bind targets of interest. In one embodiment the compounds bind ions, such as metal ions.

A compound, or a protonate or salt thereof, having the formula of:

(Continued)

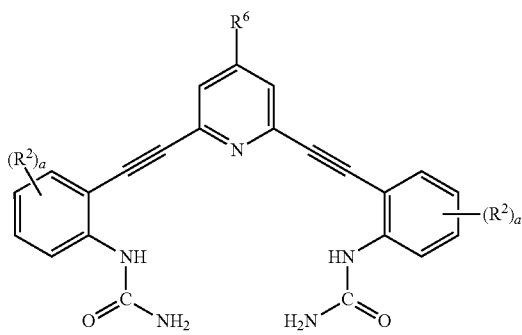

Formula IIa
wherein $R^6$ is an aminoalkoxy, alkylamino, nitro or —$NH_2$;
n is 1 or 2;
each $R^2$ is independently selected from an optionally substituted alkyl, halogen, optionally substituted alkoxy, optionally substituted carboxyl, or amide;
a is 0 to 4.

8 Claims, 2 Drawing Sheets

(51) Int. Cl.

| | |
|---|---|
| C07D 213/74 | (2006.01) |
| G01N 33/18 | (2006.01) |
| C07D 213/36 | (2006.01) |
| C07D 213/56 | (2006.01) |
| C07D 207/335 | (2006.01) |
| C07D 213/40 | (2006.01) |
| C07D 213/68 | (2006.01) |
| G01N 31/22 | (2006.01) |

(52) U.S. Cl.
CPC ......... *C07D 213/40* (2013.01); *C07D 213/56* (2013.01); *C07D 213/68* (2013.01); *C07D 213/74* (2013.01); *G01N 31/22* (2013.01); *Y10T 436/193333* (2015.01)

(56) References Cited

U.S. PATENT DOCUMENTS

2008/0167472 A1  7/2008  Haley et al.
2011/0015396 A1  1/2011  Haley et al.

OTHER PUBLICATIONS

Berryman et al., "Water and hydrogen halides serve the same structural role in a series of 2+2 hydrogen-bonded dimers based on 2,6-bis(2-anilinoethynyl)pyridine sulfonamide receptors," *Angewandte Chemie International Edition*, 47(1): 117-120, 2008.
Butler et al., "Bipyridylacetylenes 1: the synthesis of some bipyridylacetylenes via the palladium-catalyzed coupling of acetylenes with 2,2'-dibromobipyridyl, and the single crystal X-ray structure of 6,6'-bisphenylethynyl-2,2'-bipyridine," *Can. J. Chem.* 69:1117-1123, Jan. 1991.
Carroll et al., "Protonation activates anion binding and alters binding selectivity in new inherently fluorescent 2,6-bis(2-anilinoethynyl)pyridine bisureas," *Chemical Communications*, pp. 2520-2522, Mar. 27, 2009.
Carroll et al., "Anion-dependent fluorescence in bis(anilinoethynyl)pyridine derivatives: switchable ON-OFF and OFF-ON responses," *Chemical Communications* 47:5539-5541, 2011.
Dash et al., "G-quadruplex recognition by bis-indole carboxamides," *Chemical Communications*, pp. 3055-3057, Jun. 5, 2008.
Dash et al., "Diarylethynyl Amides That Recognize the Parallel Conformation of Genomic Promoter DNA G-Quadruplexrd," *Journal of the American Chemical Society*, 130(47): 15950-15956, Nov. 4, 2008.
Droz et al., "Synthesis of highly-functionalised, optically active disaccharide receptors by sequential aryl-alkyne cross-and oxidative acetylenic homo-coupling," *J. Chem. Soc., Perkin Trans.*, pp. 4224-4426, Nov. 10, 2000.
Engle et al., "Synthesis and Optoelectric Properties of 2,6-Bis(2-anilino-etynyl)pyridine Scaffolds," *Chem. Sci.*, 3:1105-1110, 2012.
Ferrara et al., "Synthesis and Characterization of a Copper(I) Triflate Complex of 1,2:5,6:9,10-Tribenzocyclododeca-1,5,9-triene-3,7,11-triyne," *Organometallics*, 6(3):676-678, 1987.
Ferrara et al., "Synthesis and Characterization of the First Transition-Metal Complex of 1,2:5,6:9.10-Tribenzocyclododeca-1,5,9-triene-3,7,11-triyne," *J. Am. Chem. Soc.*, 107(23): 6719-6721, 1985.
Gerhardt et al., "Controlling polymer properties through dynamic metal-ligand interactions: supramolecular cruciforms made easy," *Chem. Eur. J.*, 13(16):4467-4474, May 25, 2007.
Gerhardt et al., "Supramolecular cruciforms." *Chemical Communications*, No. 20, pp. 2141-2143, Mar. 21, 2006.
Hauck et al., "Phenothiazine Cruciforms: Synthesis and Metallochromic Properties," *Journal of Organic Chemistry*, No. 72. pp. 6714-6725, May 3, 2007,
Jia et al., "Novel Phosphorescent Cyclometalated Orgatonin(IV) and Organolead(IV) Complexes of 2,6-Bis(2'-indolyl)pyridine and 2,6-Bis[2'-(7-azaindolyl)]pyridine," *Organometallics*, No. 22, pp. 4070-4078. May 29, 2003.
Johnson et al., "Aryl-Acetylene Scaffolding as Receptors in Supramolecular Chemistry," presentation through Department of Chemistry and Materials Science Institute of the University of Oregon; 2007; 26 pages.
Johnson et al., "Synthesis and characterization of pyridine- and thiophene-based platinacyclenes," *Journal of Organometallic Chemistry*, No. 691, pp. 413-421, Oct. 25, 2005.
Leininger et al., "Self-Assembly of Discrete Cyclic Nanostructures Mediated by Transition Metals," *Chem. Rev.*, 100(3): 853-908, Feb. 4, 2000.
McGrier et al., "Hydroxy-cruciforms," *Chemical Communications*, pp. 2127-2129, May 1, 2007.
Pucher et al., "Structure-Activity Relationship D-II-A-II-D-Based Photoinitiators for the Two-Photon-Induced Photopolymerization Process," *Macromolecules*, 42(17): 6519-6528, Aug. 6, 2009.
Walters et al., "Experimental Studies of Light-Induced Charge Transfer and Charge Redistribution in (X2-Bipyridine)ReI(CO)3C1 Complexes," *Inorganic Chemistry*, 41(11): 2909-2919, Apr. 19, 2002.
Wilson et al., "Switching of Intramolecular Charge Transfer in Cruciforms: Metal Ion Sensing," *Journal of the American Chemical Society*, 127(12): 4124-4125, Mar. 2, 2005.
Zucchero et al., "Cruciforms as functional fluorophores: Response to protons and selected metal ions," *Journal of the American Chemical Society*, 128(36): 11872-11881, Aug. 19, 2006.
European Search Report in application No. 14743478.1-1501, dated Sep. 7, 2016, 6 pages.
European Claims in application No. 14743478.1-1501, dated Sep. 2016, 6 pages.

* cited by examiner

PHENYLACETYLENES

PRIORITY CLAIM

This is the U.S. National Stage of International Application No. PCT/US2014/012303, filed Jan. 21, 2014 which was published in English under PCT Article 21(2), which in turn claims the benefit of U.S. Patent Application No. 61/755,773, filed Jan. 23, 2013, which is incorporated by reference in its entirety.

ACKNOWLEDGMENT OF GOVERNMENT SUPPORT

This invention was made with government support under grant number R01-GM087398 awarded by National Institutes of Health. The government has certain rights in the invention.

BACKGROUND

The synthesis of new molecules designed to bind or sense and report the presence of a particular substrate is an area of chemistry that is attracting attention. There exists a general lack of ligand-specific host molecules, such as specific hosts for toxic ions and small molecules of interest. There also is a dearth of specific hosts that report binding events, for example by exhibiting a spectral shift upon binding, such as an altered fluorescent response. In fact, structures of fluorescent coordination complexes are generally poorly understood, which makes the rational design of functional hosts and sensors a challenging undertaking.

Interest in supramolecular sensors for the detection of analytes has received considerable attention over the past two decades. Such systems exploit non-covalent interactions between a guest molecule and a host molecule to induce a change in the host (e.g. NMR shift, color, fluorescence, electrochemical behavior etc.). These systems are advantageous when compared to chemodosimeters because these non-covalent interactions are reversible, which allows one to monitor an analyte dynamically. Arguably the most powerful of these sensors exploit a fluorescence/colorimetric change due to their inherent sensitivity.

The detection of ionic species, in particular the selective detection of a particular ionic species in the presence of another is difficult. The detection of anionic species is a particular challenge, as anions are difficult to bind and are generally larger than cations leading to a smaller charge-to-radius ratio.

SUMMARY

Disclosed herein are host or receptor compounds that bind targets of interest. In one embodiment the compounds bind ions, such as metal ions. In particular, toxic metal ions, including anions and cations are bound by embodiments of the disclosed host compounds.

Disclosed herein in one embodiment is a compound, or a protonate or salt thereof, having the formula of:

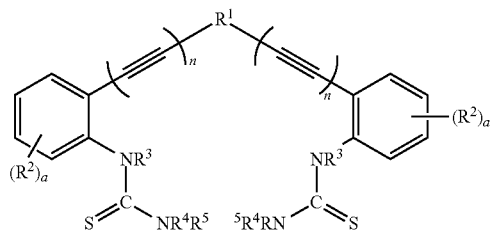

Formula I wherein $R^1$ is an optionally substituted aromatic group;
n is 1 or 2;
each $R^2$ is independently selected from an optionally substituted alkyl, halogen, optionally substituted alkoxy, optionally substituted carboxyl, or amide;
a is 0 to 4;
$R^3$ is H or an optionally substituted alkyl;
each $R^4$ and $R^5$ is independently selected from H, optionally substituted alkyl, acyl, optionally substituted aralkyl, optionally substituted aryl, or —C(O)$R^8$; and
$R^8$ is H, alkyl, aralkyl or aryl.

Disclosed herein in a further embodiment is a compound, or a protonate or salt thereof, having the formula of:

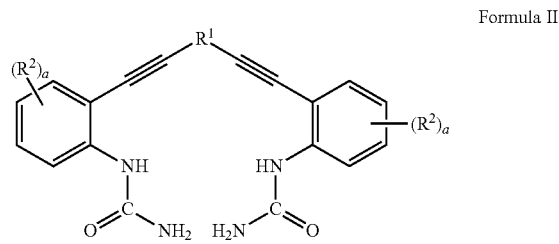

Formula II wherein $R^1$ is an aromatic group substituted with an aminoalkoxy, alkylamino, nitro, or —NH$_2$;
each $R^2$ is independently selected from an optionally substituted alkyl, halogen, optionally substituted alkoxy, optionally substituted carboxyl, or amide; and
a is 0 to 4.

Disclosed herein in an additional embodiment is a compound, or a protonate or salt thereof, having the formula of:

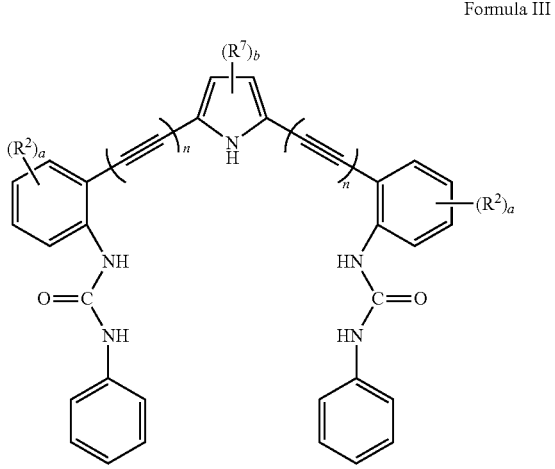

Formula III wherein each $R^7$ is independently alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

b is 0 to 2;

n is 1 or 2;

each $R^2$ is independently selected from an optionally substituted alkyl, halogen, optionally substituted alkoxy, optionally substituted carboxyl, or amide; and a is 0 to 4.

Further disclosed herein is a method for detecting for the presence of a target of interest in a system, comprising contacting a compound as disclosed herein with a sample from the system.

Exemplary compounds exhibit shifts in their spectral properties upon ligand binding. Accordingly, also disclosed are methods for using the host compounds to detect targets of interest, including neutral, cationic and anionic targets.

The foregoing will become more apparent from the following detailed description, which proceeds with reference to the accompanying figures.

DETAILED DESCRIPTION

Figure 1:
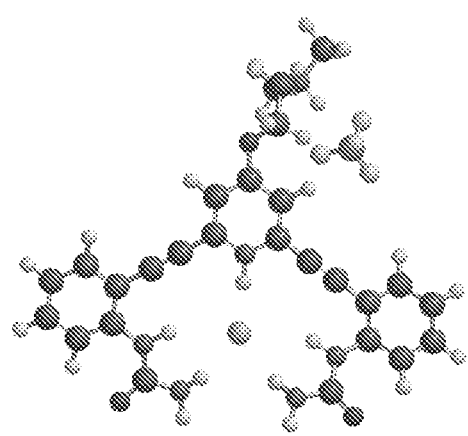
FIG. 1 illustrates a complex of $2H5^+.Cl^-.BF_4^-$ showing the proposed penta-coordinate hydrogen bonding framework.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Acyl" refers group of the formula RC(O)— wherein R is an organic group.

The term "aliphatic" includes alkyl, alkenyl, alkynyl, halogenated alkyl and cycloalkyl groups as described above. A "lower aliphatic" group is a branched or unbranched aliphatic group having from 1 to 10 carbon atoms.

The term "alkoxy" refers to a straight, branched or cyclic hydrocarbon configuration and combinations thereof, including from 1 to 20 carbon atoms, preferably from 1 to 10 carbon atoms, more preferably from 1 to 4 carbon atoms, that includes an oxygen atom at the point of attachment. An example of an "alkoxy group" is represented by the formula —OR, where R can be an alkyl group, optionally substituted with, e.g., an alkenyl, alkynyl, aryl, aralkyl, cycloalkyl, halogenated alkyl, or heterocycloalkyl group as described herein. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers an aliphatic group that is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

The term "amide" refers to the formula —C(O)NRR', wherein R and R' independently can be a hydrogen, alkyl, alkenyl, alkynyl, aryl, aralkyl, cycloalkyl, halogenated alkyl, or heterocycloalkyl group described above.

The term "aralkyl" refers to an alkyl group that is substituted with one or more aryl groups (described below). A particular example of an aralkyl group is a benzyl group.

The term "aryl" refers to any carbon-based aromatic group including, but not limited to, phenyl, naphthyl, etc. The term "aromatic" also includes "heteroaryl groups," which are defined as aromatic groups that have at least one heteroatom incorporated within the ring of the aromatic group. Examples of heteroatoms include, but are not limited to, nitrogen, oxygen, sulfur, and phosphorus. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine. "Carbonyloxy" refers to a group of the —OC(O)R where R is an aliphatic (e.g., alkyl) or aromatic (e.g., aryl) group.

"Carbonate" refers to a group of the formula —OC(O)O—. "Substituted carbonate" refers to a group of the formula —OC(O)OR. Likewise, as used herein the term "carbamate" refers to a group of the formula —OC(O)N(R)—, wherein R is H, or an aliphatic group, such as a lower alkyl group or an aralkyl group.

"Carboxyl" refers to a —COOH radical. Substituted carboxyl refers to —COOR where R is aliphatic, heteroaliphatic, alkyl, heteroalkyl, or a carboxylic acid or ester.

"Optional" or "optionally" means that the subsequently described event or circumstance can but need not occur, and that the description includes instances where said event or circumstance occurs and instances where it does not. Optionally substituted groups, such as "substituted alkyl," refers to groups, such as an alkyl group, having from 1-5 substituents, typically from 1-3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, optionally substituted heteroaryl, optionally substituted heterocyclyl, hydroxy, thiol and thioalkoxy.

The term "phosphoryl" refers to moieties of the formula —P(O)OR—, wherein R may be H, an aliphatic or aromatic moiety, a cation or a lone pair of electrons. Phosphoryl moieties may be further substituted to form phosphoramidates, phosphates and phosphonates.

The term "polyether moiety" may be an oligomer (which is inclusive of dimers and higher repeating units) or a polymer. Illustrative polyether moieties include those derived from an aliphatic polyether (e.g., paraformaldehyde, polyethylene glycol (PEG), polypropylene glycol, and polytetramethylene glycol, and those derived from an aromatic polyether (e.g., polyphenyl ether or poly(p-phenylene oxide)). A preferred polyether moiety is derived from PEG, also referred to herein as a poly(ethylene oxide). The PEG may be a straight chain PEG or a branched PEG. PEG is also inclusive of methoxypolyethylene glycol. In certain embodiments, the number of repeating ethylene oxide units in the PEG moiety may range from 2 to 50, more particularly from 2 to 10. The polyether moiety may be covalently bonded to the core motif via PEGylation procedures.

The term "sulfonyl" refers to the radical —SO$_2$—. The sulfonyl group can be further substituted with a variety of groups to form, for example, sulfonic acids, sulfonamides, sulfonate esters and sulfones.

Protected derivatives of the disclosed compound also are contemplated. A variety of suitable protecting groups for use with the disclosed compounds are disclosed in Greene and Wuts Protective Groups in Organic Synthesis; 3rd Ed.; John Wiley & Sons, New York, 1999.

It is understood that substituents and substitution patterns of the compounds described herein can be selected by one of ordinary skill in the art to provide compounds that are chemically stable and that can be readily synthesized by techniques known in the art and further by the methods set forth in this disclosure.

The disclosed host compounds are useful, inter alia, as ion binding compounds. By way of example, specific anions bound by the disclosed compounds include, but are not limited to, toxic metal anions, halide anions, carboxylates, phosphates, sulfates, oxalates, terephthalates, phospholipids, nucleotides, oligonucleotides, DNA, RNA, anionic polyoxometalates, or oxoanions such as pertechnetate.

The structural formulas provided herein include salts of the illustrated compounds. Such salts can be formed when disclosed host compounds possess at least one basic group that can form acid-base salts with acids. Examples of basic groups present in exemplary disclosed host compounds include amino groups or imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

Similarly, salts can be formed when disclosed host compounds possess at least one acidic group that can form acid-base salts with bases. Examples of acidic groups present in exemplary disclosed host compounds include carboxylic acid moieties and sulfonamide groups. Compounds that include at least one acidic group can form an acid-base salts with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. In addition, quaternary ammonium counterions also can be used.

Additionally, the structural formulas herein are intended to cover, where applicable, solvated as well as unsolvated forms of the compounds. "Solvate" refers to a compound physically associated with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compounds, methanol associated compounds, and the like. "Hydrate" is a solvate wherein the solvent molecule(s) is/are H$_2$O. Solvate complexes may be described in shorthand form for example as (1.H$_2$O)$_2$, which refers to a hydrate, more specifically a 2+2 complex of compound 1 with water.

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

In one embodiment the compounds, or salts thereof, have the formula I:

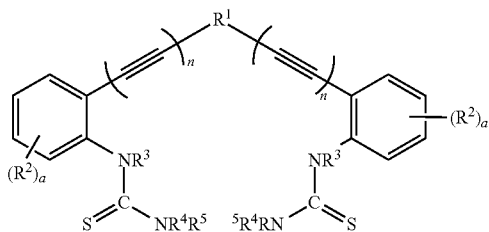

wherein R$^1$ is an optionally substituted aromatic group;
n is 1 or 2;
each R$^2$ is independently selected from an optionally substituted alkyl, halogen, optionally substituted alkoxy, optionally substituted carboxyl, or amide;
a is 0 to 4;
R$^3$ is H or an optionally substituted alkyl;
each R$^4$ and R$^5$ is independently selected from H, optionally substituted alkyl, acyl, optionally substituted aralkyl, optionally substituted aryl, or —C(O)R$^8$; and
R$^8$ is H, alkyl, aralkyl or aryl.
R$^1$ can be any aromatic group such as phenylene or a heteroaromatic group, but typically R$^1$ comprises an N-heteroaromatic group. For example, in one embodiment, $R^1$ is a pyridyl group. Additional exemplary $R^1$ groups include, without limitation, bipyridyl, pyridinyl, pyrazinyl, pyrimidinyl, pyrrole, imidazole, triazole, thiophene, thiazole, furyl and oxazolyl groups. By way of example, such $R^1$ groups can be selected from

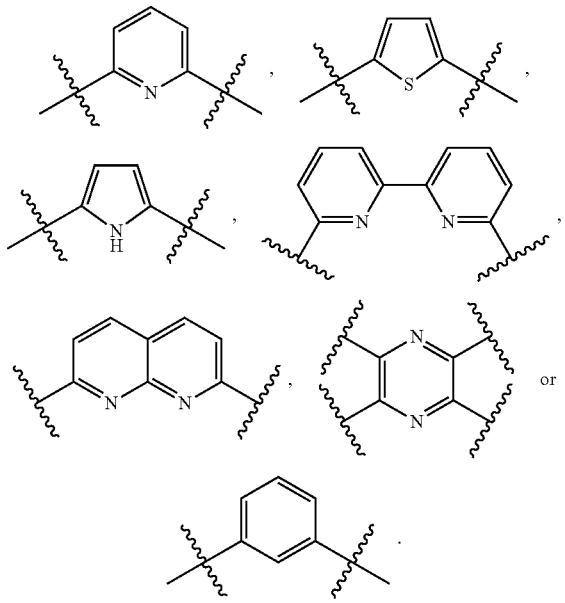

In certain embodiments, $R^1$ may be:

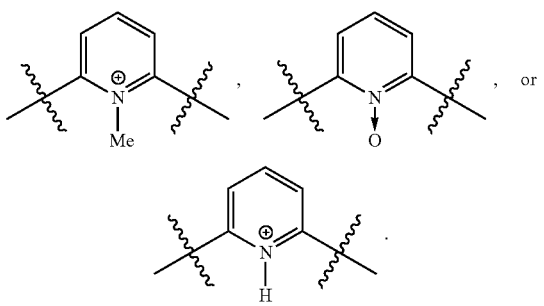

$R^1$ may be substituted with alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl.

In certain embodiments, n is 1.

In certain embodiments, $R^2$ is a lower alkyl such as methyl, ethyl, n-propyl, isopropyl, n-butyl, or tert-butyl.

In certain embodiments, a is 0. In certain embodiments, a is 1.

In certain embodiments, $R^3$ is H.

In certain embodiments, $R^4$ is H and $R^5$ is optionally substituted aryl (particularly phenyl).

Certain embodiments of the compounds of formula I have the formula Ia:

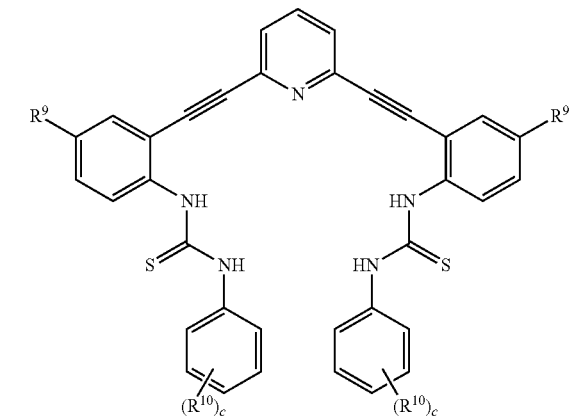

wherein $R^9$ is a lower alkyl such as methyl, ethyl, n-propyl, isopropyl, n-butyl, or tert-butyl; $R^{10}$ is independently selected from a lower alkyl, halogen, nitro, optionally substituted alkoxy, optionally substituted carboxyl, or amide; and c is 0 to 5. In certain embodiments, $R^{10}$ is a nitro. In certain embodiments, c is 1 and $R^{10}$ is in a para position relative to the thiourea moiety. In certain embodiments, $R^9$ is t-butyl, c is 1, $R^{10}$ is nitro and is in a para position relative to the thiourea moiety. In certain embodiments, $R^9$ is t-butyl, c is 1, $R^{10}$ is methoxy and is in a para position relative to the thiourea moiety. In certain embodiments, $R^9$ is methyl, ethyl, n-propyl, isopropyl, n-butyl, isobutyl, t-butyl, pentyl, hexyl, heptyl, octyl, decyl, tetradecyl, hexadecyl, eicosyl, or tetracosyl; and $R^{10}$ is methoxy, ethoxy, n-propoxy, i-propoxy, n-butoxy, i-butoxy, sec-butoxy, tert-butoxy cyclopropoxy, or cyclohexyloxy, and is in a para position relative to the thiourea moiety.

In certain embodiments the compounds of formula I are colorimetric sensors. For example, they may undergo a color change (i.e., from a first color to a second color) and/or gelation in the presence of specific anions (e.g., with halides and perchlorate). In addition, the compounds of formula I exhibit enhanced urea acidity which may lead to tighter/stronger binding to a target of interest.

In another embodiment the compounds, or salts thereof, have the formula II:

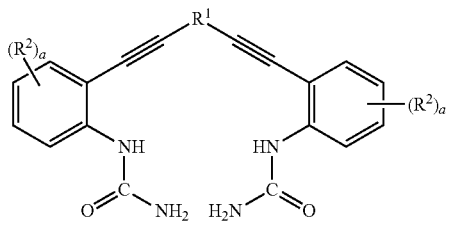

wherein $R^1$ is an aromatic group substituted with an aminoalkoxy, alkylamino, nitro or —$NH_2$;

each $R^2$ is independently selected from an optionally substituted alkyl, halogen, optionally substituted alkoxy, optionally substituted carboxyl, or amide; and a is 0 to 4.

$R^1$ can include any aromatic group such as phenylene or a heteroaromatic group, but typically $R^1$ comprises an N-heteroaromatic group. For example, in one embodiment, $R^1$ is a pyridyl group. Additional exemplary $R^1$ groups include, without limitation, bipyridyl, pyridinyl, pyrazinyl, pyrimidinyl, pyrrole, imidazole, triazole, thiophene, thiazole, furyl and oxazolyl groups. By way of example, such $R^1$ groups can be selected from

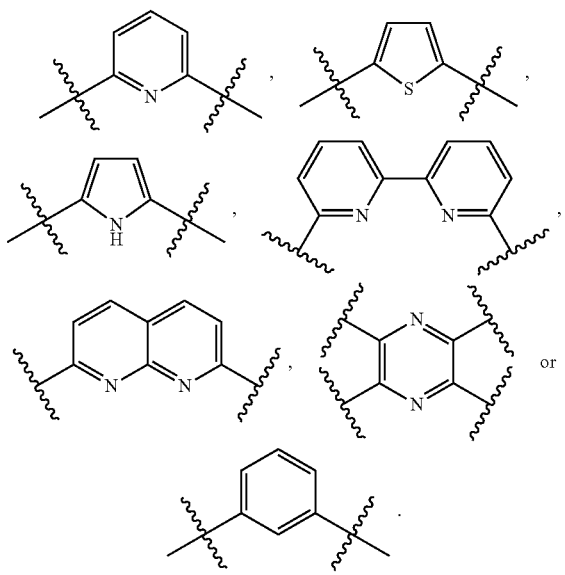

In certain embodiments, $R^1$ may be:

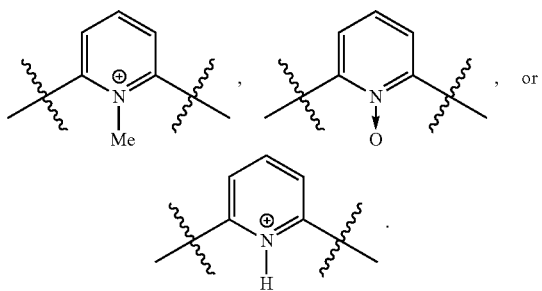

In certain embodiments a is 0. In certain embodiments a is 1, and $R^2$ is preferably in a para position relative to the terminal urea moiety.

In one embodiment the compounds, or salts thereof, have the formula IIa:

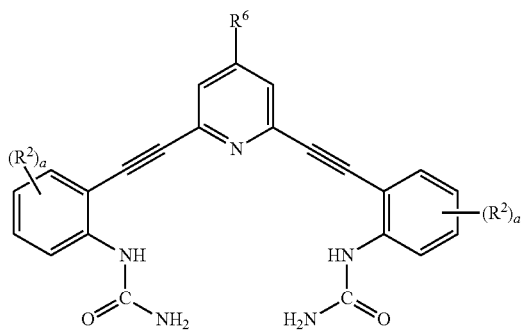

wherein $R^6$ is an aminoalkoxy, alkylamino, nitro, or —$NH_2$;

each $R^2$ is independently selected from an optionally substituted alkyl, halogen, optionally substituted alkoxy, optionally substituted carboxyl, or amide; and a is 0 to 4.

In certain embodiments $R^6$ is an aminoalkoxy such as, for example, —$O(CH_2)_d NR^{11}R^{12}$, wherein d is 1 to 10, preferably 1 to 4, more preferably 1, 2, 3 or 4; and each $R^{11}$ and $R^{12}$ are independently H or lower alkyl. In certain embodiments each of $R^{11}$ and $R^{12}$ is H or each of $R^{11}$ and $R^{12}$ is methyl.

In certain embodiments $R^6$ is an alkylamino such as, for example, —$NR^{11}R^{12}$, each $R^{11}$ and $R^{12}$ are independently H or lower alkyl, provided that at least one of $R^{11}$ or $R^{12}$ is a lower alkyl. In certain embodiments each of $R^{11}$ and $R^{12}$ is a lower alkyl such as methyl.

In certain embodiments of the compound of formula IIa, a is 0. In certain embodiments of the compound of formula IIa, a is 1, and $R^2$ is preferably in a para position relative to the terminal urea moiety.

In certain embodiments, $R^2$ is in a para position relative to the terminal urea moiety, and is selected from —C(O)OH, —C(O)NHR$^{20}$, or —C(O)OR$^{20}$, wherein $R^{20}$ is selected from H, methyl, ethyl, n-propyl, isopropyl, n-butyl, isobutyl, t-butyl, pentyl, hexyl, heptyl, octyl, decyl, tetradecyl, hexadecyl, eicosyl, or tetracosyl; a is 0 or 1; and $R^6$ is —$O(CH_2)_2N(CH_3)_2$, —$N(CH_3)_2$, or nitro.

Existing fluorescent sensors that are used for the detection of chloride anions typically undergo a fluorescent quenching mechanism. Disclosed herein is a fully organic fluorescent sensor (compound of formula II) that turns on in the presence of chloride in aqueous solvents or mixtures. For example, the compound may be used in aqueous mixtures that include an acid source such as, for example, trifluoroacetic acid, acetic acid, tetrafluoroboric acid, or formic acid. The compound may also be a fully organic fluorescent sensor that turns on in a methanol-containing mixture. In order to overcome the problem of halide quenching, an aggregation induced emission mechanism is exploited whereby host-guest complexes aggregate and subsequently fluoresce. These systems could prove to be valuable for chloride imaging and provide a proof a concept towards using aggregation induced emission to detect notoriously hard to detect analytes.

The terminal urea compounds of formula II display a fluorescence turn-on response in an aqueous environment. The terminal urea compounds of formula II are fully organic sensors that can turn "on" in water. By "fully organic" it is meant that the compounds are not inorganic-based nanoparticles, or organometallic complexes. In certain embodiments, the compounds of Formula II are selective for chloride in aqueous systems. Although not bound by any theory, it is believed that the fluorescence is turned "on" due to aggregation induced emission (AIE). Unlike most 1:1 host/guest sensors, it is believed that the compound of formula II hydrogen bonds to chloride, which causes the fluorophore to rigidify and allows for intermolecular stacking between fluorophore-guest subunits. These stacks (not the 1:1 host/guest complex itself) are highly emissive.

In a further embodiment the compounds, or salts thereof, have the formula III:

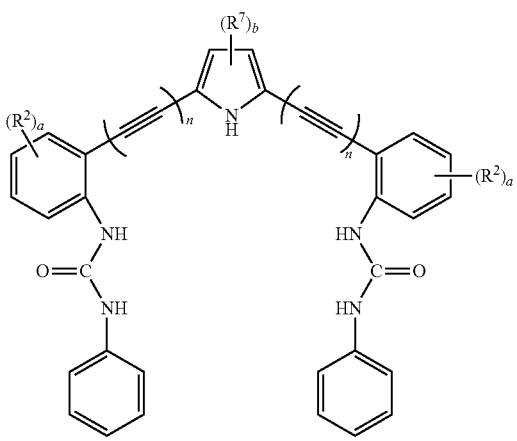

wherein each $R^7$ is independently alkyl, substituted alkyl, a polyether moiety, carboxyl, substituted carboxyl, carbamate, substituted carbonate, carbonyloxy, alkoxy, substituted alkoxy, haloalkyl, halogen, nitro, amino, aryloxy, cyano, hydroxyl, or sulfonyl;

b is 0 to 2;

n is 1 or 2;

each $R^2$ is independently selected from an optionally substituted alkyl, halogen, optionally substituted alkoxy, optionally substituted carboxyl, or amide; and a is 0 to 4.

In certain embodiments of the compound of formula III, $R^7$ is lower alkyl such as methyl, ethyl, n-propyl, isopropyl, n-butyl, or tert-butyl.

In certain embodiments of the compound of formula III, b is 0.

In certain embodiments of the compound of formula III, n is 1.

In certain embodiments of the compound of formula III, $R^2$ is lower alkyl such as methyl, ethyl, n-propyl, isopropyl, n-butyl, or tert-butyl.

In certain embodiments of the compound of formula III, a is 0. In certain embodiments of the compound of formula III, a is 1, and $R^2$ is preferably in a para position relative to the terminal phenylurea moiety, particularly a lower alkyl such as methyl, ethyl, n-propyl, isopropyl, n-butyl, or tert-butyl.

In certain embodiments of the compound of formula III, a is 1; $R^2$ is in a para position relative to the terminal phenylurea moiety, and is methyl, ethyl, n-propyl, isopropyl, n-butyl, or tert-butyl; n is 1; b is 1; and $R^7$ is methyl, ethyl, n-propyl, isopropyl, n-butyl, tert-butyl, —O(CH$_2$)$_2$N(CH$_3$)$_2$, —N(CH$_3$)$_2$, or nitro.

In certain embodiments of the compound of formula III, a is 1; $R^2$ is in a para position relative to the terminal phenylurea moiety, and is methyl, ethyl, n-propyl, isopropyl, n-butyl, or tert-butyl; n is 1; and b is 0.

In certain embodiments, the compounds of formula III provide a neutral core that presents an acidic proton to the core for anion binding meaning that the compounds of formula III do not require protonation for binding.

The compounds disclosed herein are inclusive of their protonated forms, salt forms, and N-oxide forms.

The disclosed host compounds are useful for binding and/or detecting ligands, in particular ionic ligands, including cationic and anionic ligands. The ligands may be inorganic or organic, but generally are inorganic. Typically, for binding anionic ligands, host compounds are protonated. Particular examples of anionic ligands bound and/or recognized by the disclosed host compounds include, without limitation sulfate, hydrogen sulfate, perchlorate or nitrate. Exemplary host compounds exhibit ligand binding selectivity or recognition. The host compounds may exhibit selectivity in binding of the ligand or reporting of a ligand's presence. For example, a spectral property of a host compound, such as fluorescence, may shift upon binding certain ligands, but not others. Examples of the disclosed host compounds have been designed to bind to salts containing particular metals, particularly toxic metals, including without limitation Pb, As, Zn, U, Ca, Cd and Hg.

It has been demonstrated for exemplary compounds disclosed herein that the spectral properties, such as the UV-Vis spectra shift noticeably upon binding of different guests. For example, the extended conjugation inherent in 2,6-bis(2-anilinoethynyl)pyridines derivatives produces distinct emission properties that will be used to monitor interactions with guest molecules. Exemplary compounds can distinguish between different anionic guests such as between Cl$^-$, which induces a shift in the UV-vis spectra of certain compounds, and Br$^-$, which does not induce such shifts.

This discriminatory ability is most marked when the receptor is protonated. This indicates that these specific receptors can discriminate between different guests and are pH sensitive and can be tailored for use in solutions of specific acidity.

EXAMPLES

A synthesis scheme for an example of a compound of formula I is shown below:

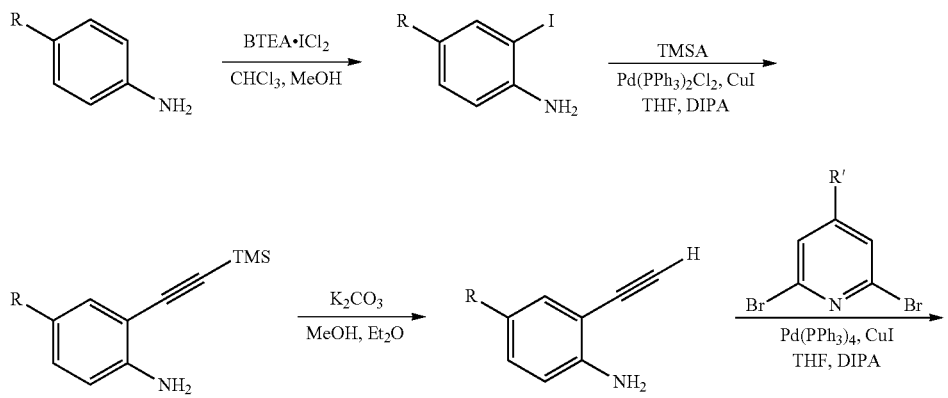

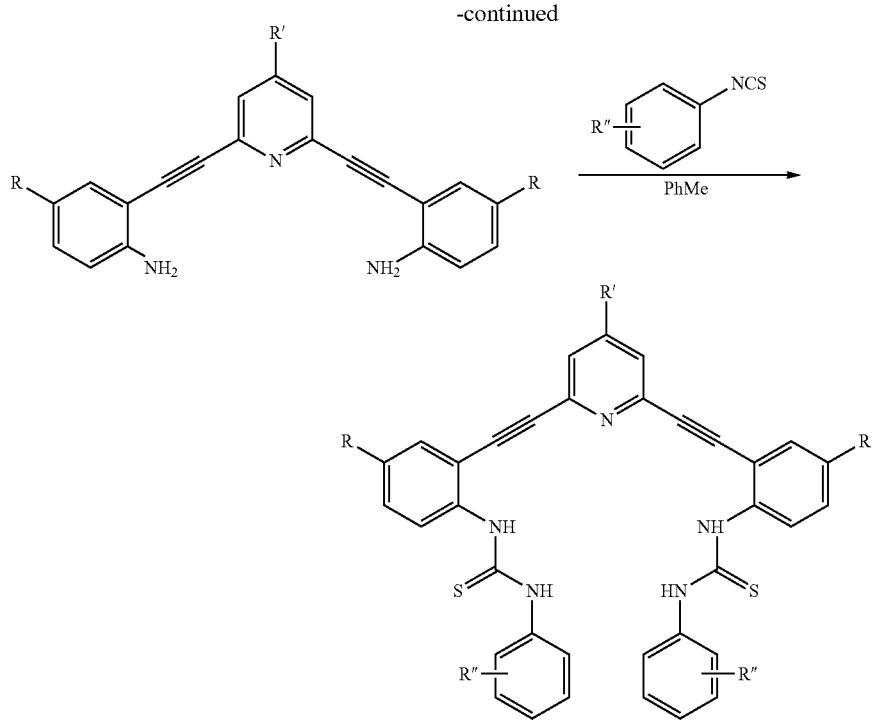
Alternate route to main core scaffold:
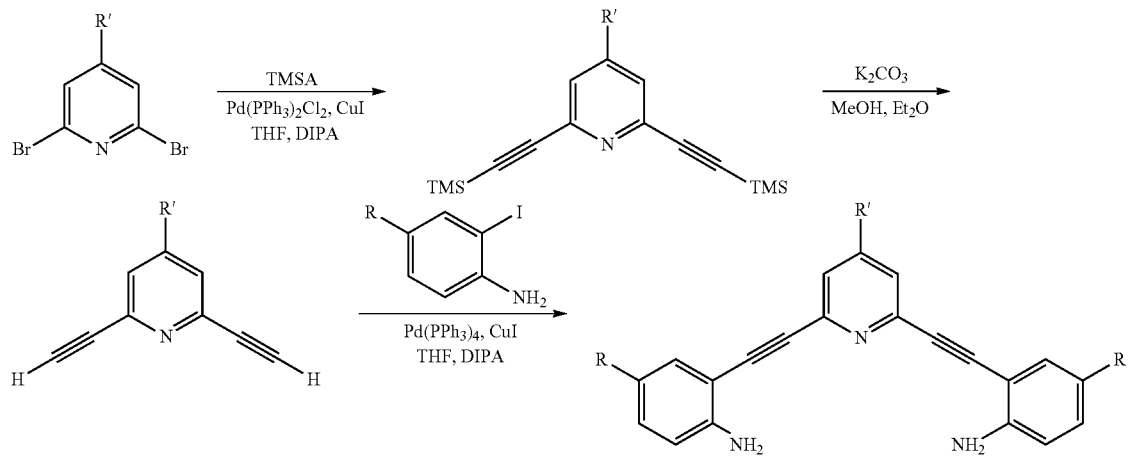
A specific compound may be synthesized as follows:
-continued
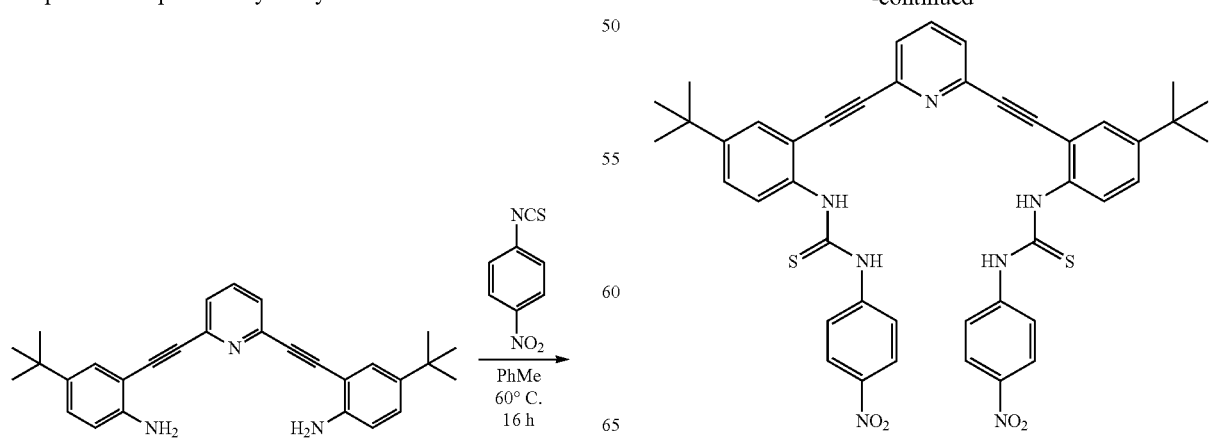

The resulting product was a vibrant orange color (when protonated with HBF$_4$). The product underwent a color change when tetrabutyl ammonium salts of the following anions were added to HBF$_4$ protonated product in acetonitrile: Cl$^-$, Br$^-$, I$^-$, ClO$_4^-$, AcO$^-$, NO$_3^-$, H$_2$PO$_4^-$.

A synthesis scheme for an example of a compound of formula II is shown below:

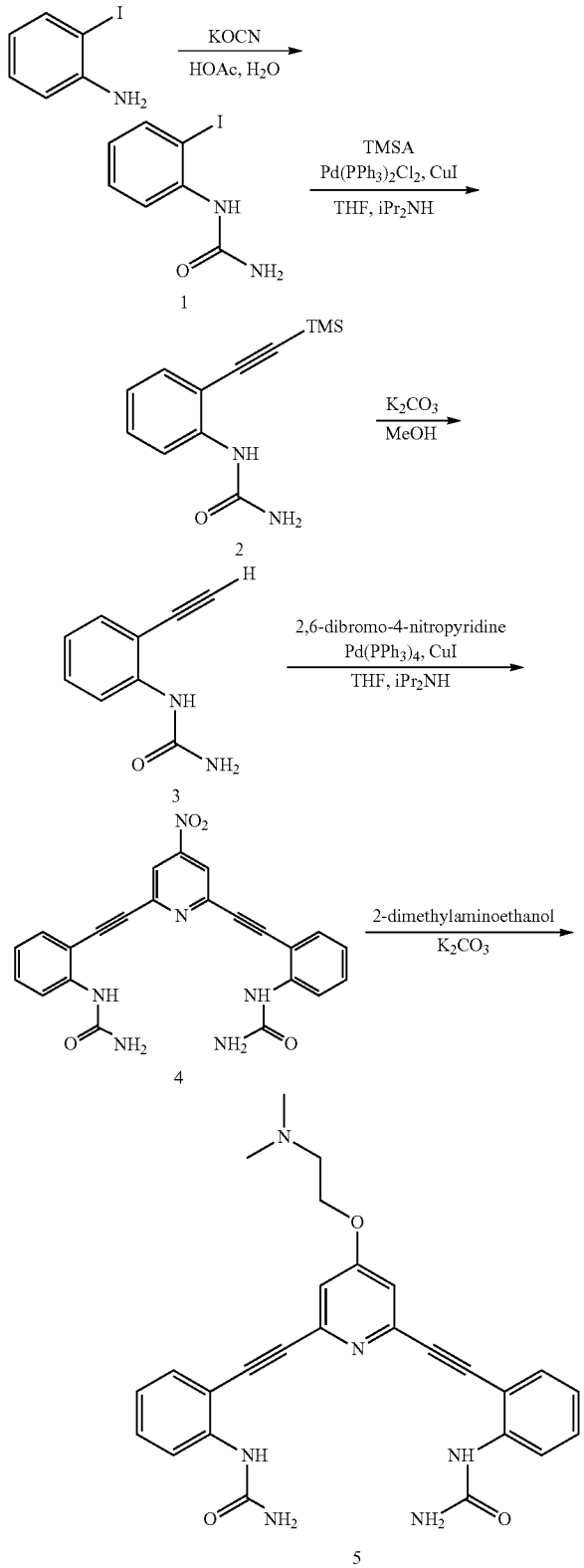

First, 2-iodoaniline is reacted with potassium cyanate to afford the ureido-functionalized intermediate 1. Compound 1 is then ethynylated using standard Sonogashira cross coupling techniques giving the TMS-protected intermediate 2. Deprotection of 2 is achieved using potassium carbonate in methanol and the resulting product 3 is coupled to 2,6-dibromo-4-nitropyridine using standard Sonogashira cross coupling techniques. Compound 4 is then reacted with 2-dimethylaminoethanol and potassium carbonate to yield the desired product 5 in modest yields.

Compound 5 is soluble in water when protonated. For these studies samples were prepared as their corresponding trifluoroacetic acid salts. A 500 μM stock solution of 5 was prepared using 1% TFA (aqueous). This stock solution was then divided into 10×1 mL aliquots. To each aliquot was added a different sodium salt (500 fold excess in relation to the host).

Figure 2:
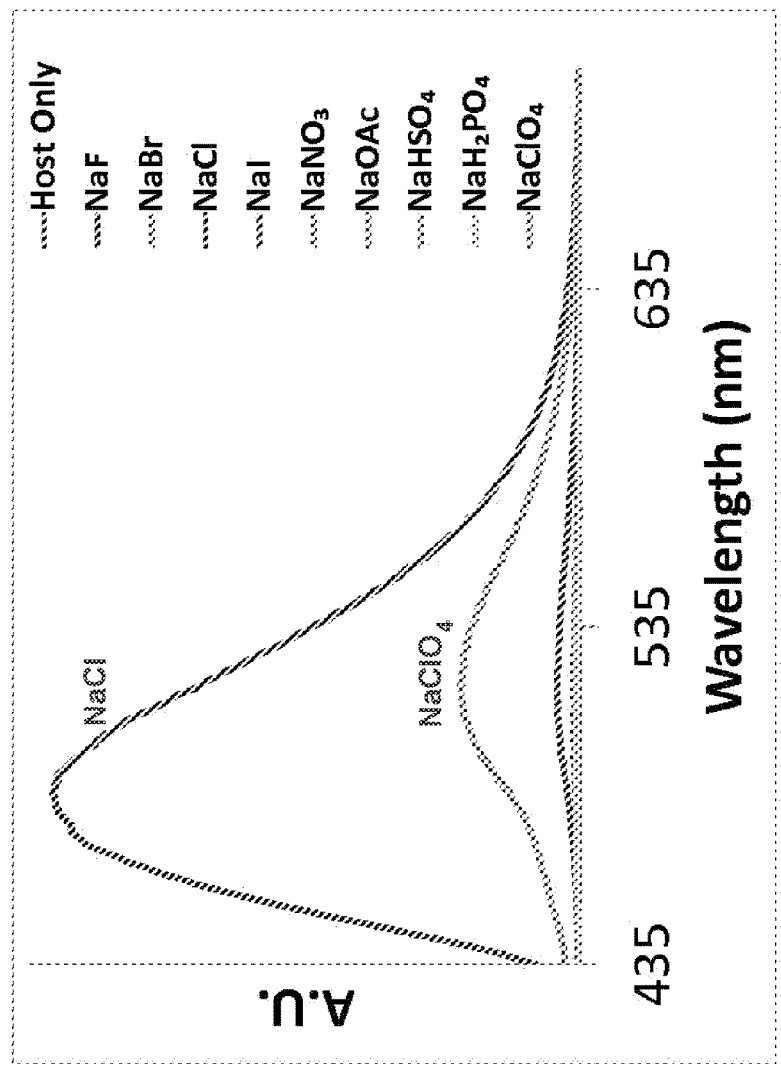
FIG. 2 depicts fluorescence emission spectra of compound 5 in $H_2O$/1% TFA while in the presence of various sodium salts.

The most immediate observation was that many of the solutions became opaque upon addition of a sodium salt. Upon examination using a handheld, 365 nm UV-lamp it became apparent that the cloudy solutions were also fluorescent (FIG. 2). Furthermore, it was noticed that the solution containing NaCl fluoresced a very distinct blue-green color. A noticeable feature is that this sensor appears to be selective for chloride over other halides and other common interferents. For example, when samples are excited at 425 nm only chloride (and to a much lesser extent perchlorate) fluoresce. This sensor takes advantage of AIE in order to overcome this obstacle.

Remarkably, this aggregation behavior does not follow the anticipated Hoffmeister series indicating that the fluorescence turn-on is not simply due to a salting out effect, but rather is due to a specific chloride-host interaction. Although not bound by any theory, it is believed that when a suitable guest is present it binds inside of the host via a penta-coordinate hydrogen bond framework leading to a restriction of rotation. With the molecule locked in a rigid conformation it aggregates, and the resulting aggregates fluoresce. When a guest is present that doesn't fit as well aggregation may occur, but fluorescence features are significantly diminished.

In order to investigate relative binding affinities for various salts $^1$H NMR titrations were performed with the TFA protonated host in DMSO-d6/0.5% H$_2$O. While these titration are not a direct comparison to aqueous systems shown in FIG. 2 they provide evidence that compound 5 preferentially binds Cl$^-$ over other anions (Table 1).

TABLE 1

| Tetrabutylammonium Salt | Binding Constant (M$^{-1}$) * |
|---|---|
| TBACl | 162 |
| TBABr | 26 |
| TBAI | — |
| TBANO$_3$ | — |
| TBAHSO$_4$ | — |
| TBAH$_2$PO$_4$ | — |
| TBAClO$_4$ | — |
| TBAOAc | Unknown |

Other compounds disclosed herein may be synthesized as shown below:

Scheme 1
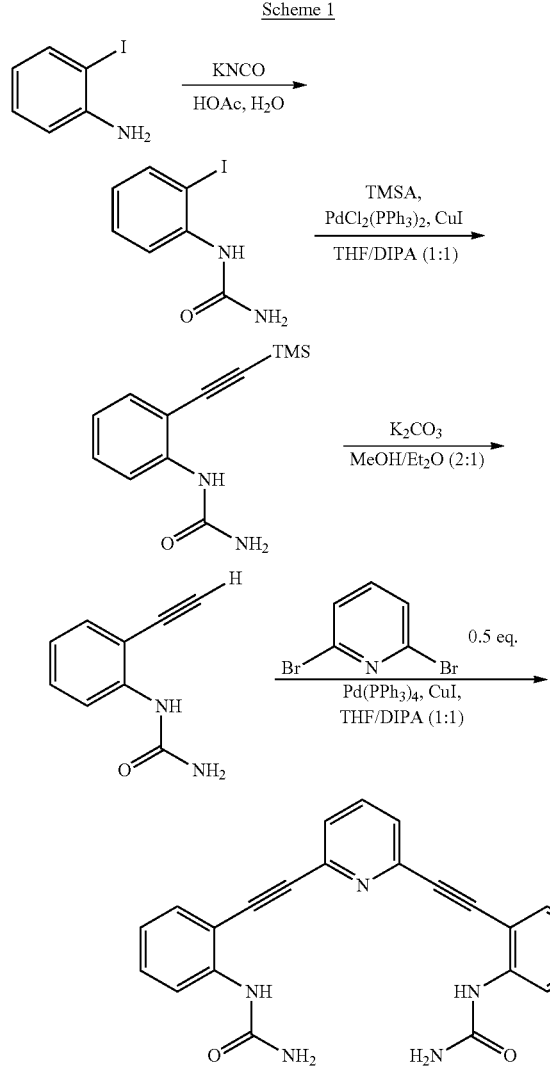
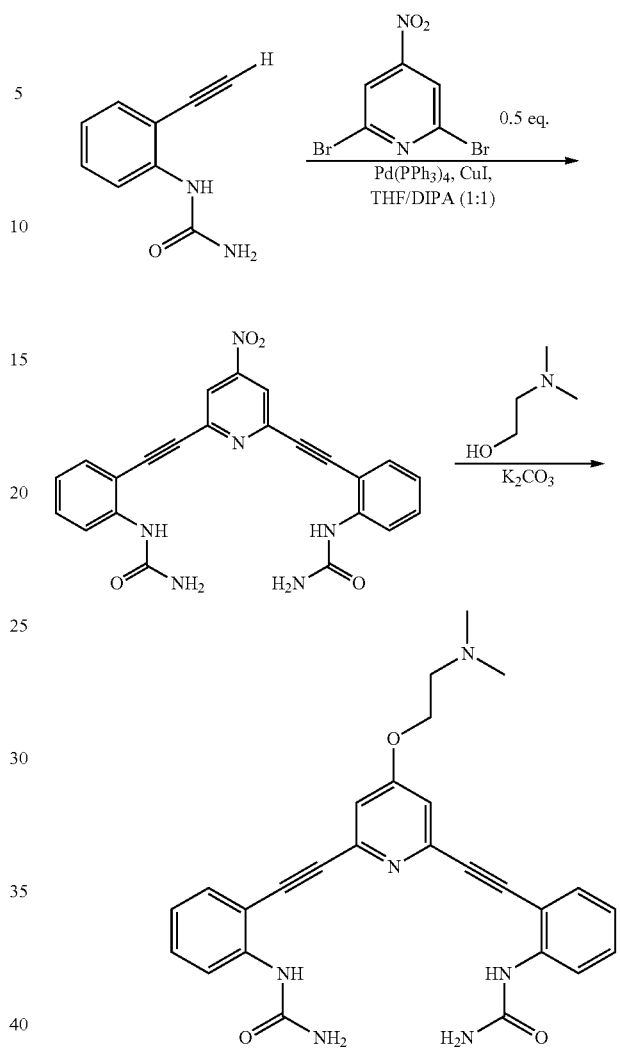
Scheme 2
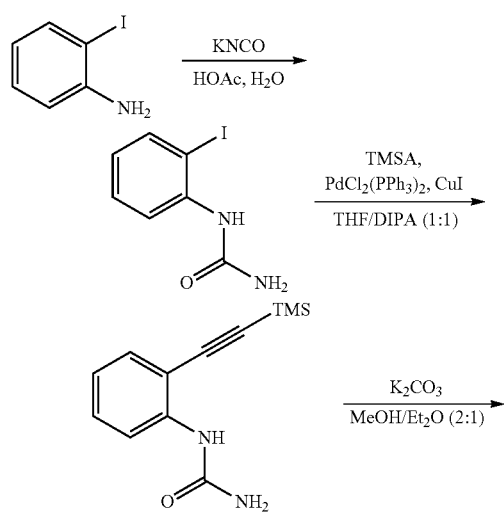
Scheme 3
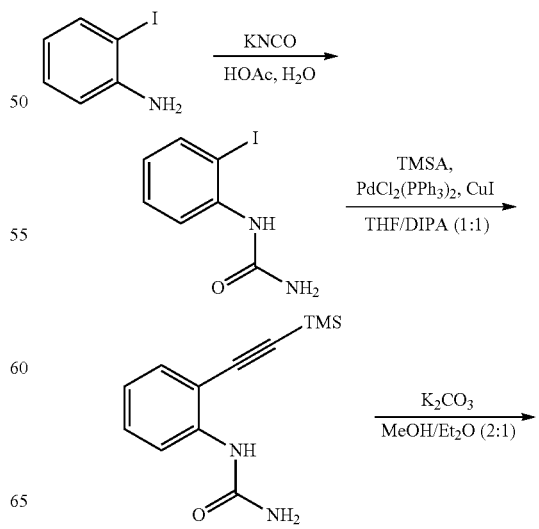

19
-continued
20
-continued
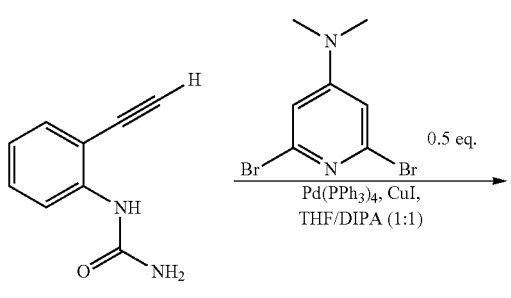
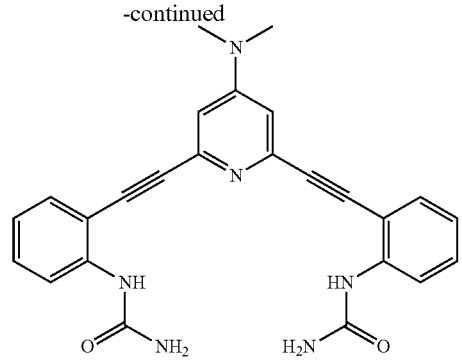
Scheme 4
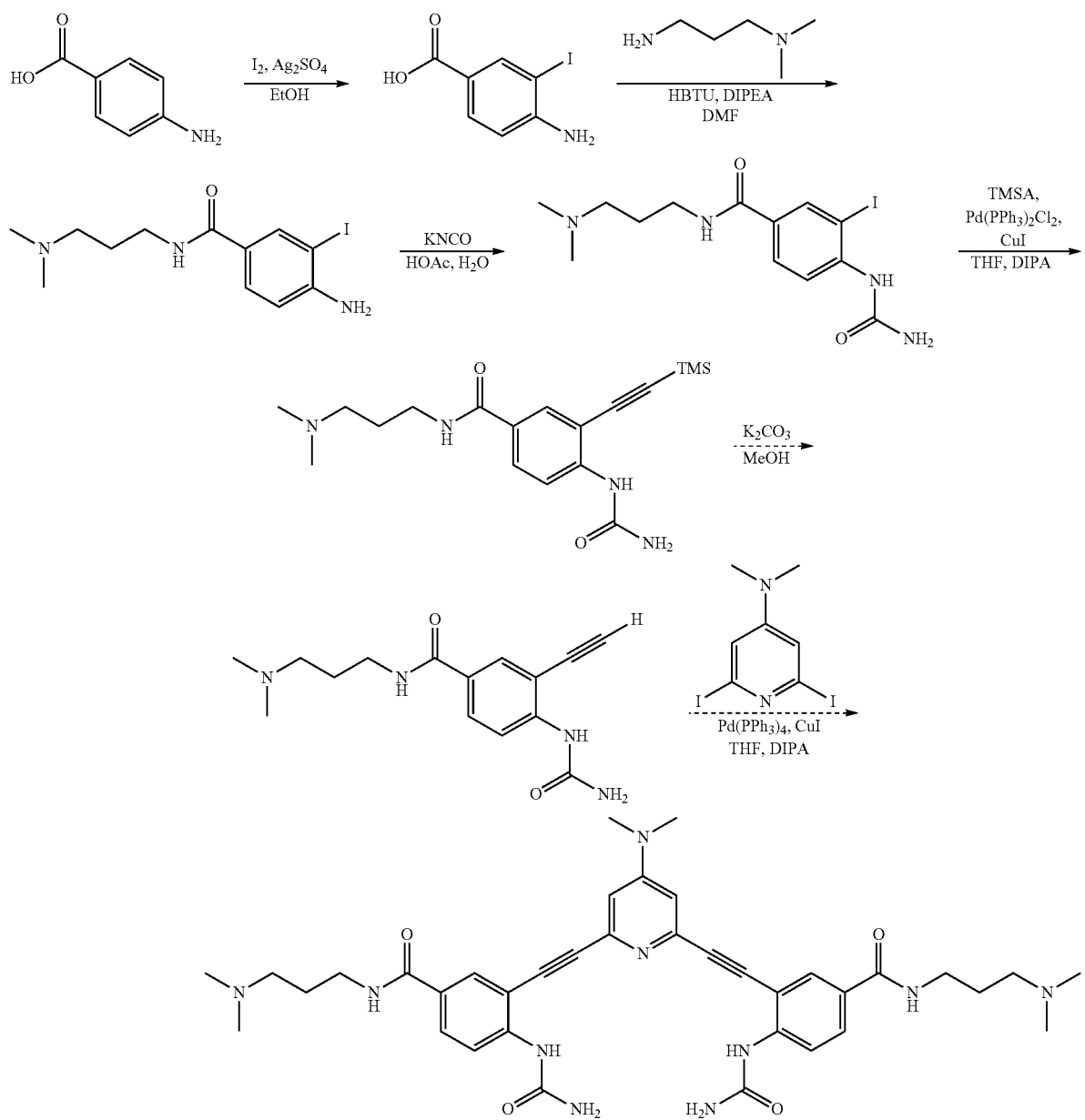

In view of the many possible embodiments to which the principles of the disclosed compositions and methods may be applied, it should be recognized that the illustrated embodiments are only preferred examples of the invention and should not be taken as limiting the scope of the invention.

What is claimed is:

1. A compound, or a protonate or salt thereof, having the formula of:

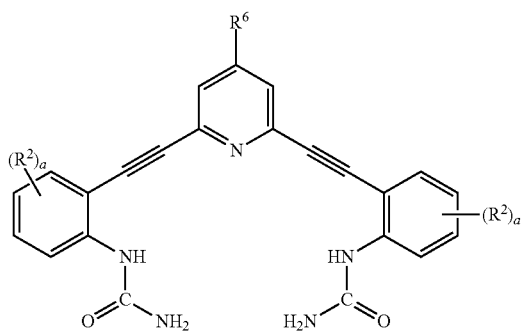

Formula IIa wherein $R^6$ is an aminoalkoxy, alkylamino, nitro or —$NH_2$;

each $R^2$ is independently selected from an optionally substituted alkyl, halogen, optionally substituted alkoxy, optionally substituted carboxyl, or amide; and a is 0 to 4.

2. The compound of claim 1, wherein $R^6$ is —O$(CH_2)_d NR^{11}R^{12}$, wherein d is 1 to 10; and each $R^{11}$ and $R^{12}$ is independently H or lower alkyl.

3. The compound of claim 2, wherein each of $R^{11}$ and $R^{12}$ is methyl, ethyl, n-propyl, isopropyl, n-butyl, isobutyl, or tert-butyl.

4. The compound of claim 2, wherein each of $R^{11}$ and $R^{12}$ is H.

5. The compound of claim 2, wherein each of $R^{11}$ and $R^{12}$ is methyl.

6. The compound of claim 2, wherein d is 2.

7. The compound of claim 1, wherein a is 0.

8. The compound of claim 1, wherein $R^2$ is methyl, ethyl, n-propyl, isopropyl, n-butyl, isobutyl, or tert-butyl.

* * * * *